US010329219B2

(12) United States Patent
Suriye et al.

(10) Patent No.: US 10,329,219 B2
(45) Date of Patent: Jun. 25, 2019

(54) PROCESS FOR CONVERTING PARAFFIN TO OLEFIN AND CATALYST FOR USE THEREIN

(71) Applicant: SCG CHEMICALS COMPANY LIMITED, Bangkok (TH)

(72) Inventors: Kongkiat Suriye, Bangkok (TH); Wuttithep Jareewatchara, Bangkok (TH); Pruphanya Lekngam, Bangkok (TH); Anuwat Nonkhamwong, Bangkok (TH); Kesada Sutthiumporn, Bangkok (TH)

(73) Assignee: SCG CHEMICALS COMPANY LIMITED, Bangkok (TH)

( * ) Notice: Subject to any disclaimer, the term of this patent is extended or adjusted under 35 U.S.C. 154(b) by 3 days.

(21) Appl. No.: 14/782,457

(22) PCT Filed: Mar. 28, 2014

(86) PCT No.: PCT/TH2014/000012
§ 371 (c)(1),
(2) Date: Oct. 5, 2015

(87) PCT Pub. No.: WO2014/163590
PCT Pub. Date: Oct. 9, 2014

(65) Prior Publication Data
US 2016/0326069 A1 Nov. 10, 2016
US 2017/0190639 A9 Jul. 6, 2017

(30) Foreign Application Priority Data
Apr. 3, 2013 (EP) .................................... 13162080

(51) Int. Cl.
C07C 5/333 (2006.01)
B01J 23/24 (2006.01)
B01J 21/10 (2006.01)
B01J 23/30 (2006.01)
C07C 6/04 (2006.01)
B01J 38/02 (2006.01)
B01J 38/12 (2006.01)
B01J 35/00 (2006.01)
B01J 21/08 (2006.01)
B01J 23/92 (2006.01)
B01J 29/08 (2006.01)
B01J 29/90 (2006.01)
B01J 37/08 (2006.01)
B01J 37/18 (2006.01)

(52) U.S. Cl.
CPC ............ *C07C 5/3335* (2013.01); *B01J 21/08* (2013.01); *B01J 21/10* (2013.01); *B01J 23/30* (2013.01); *B01J 23/92* (2013.01); *B01J 29/084* (2013.01); *B01J 29/90* (2013.01); *B01J 35/0006* (2013.01); *B01J 37/08* (2013.01); *B01J 37/18* (2013.01); *B01J 38/02* (2013.01); *B01J 38/12* (2013.01); *C07C 5/3332* (2013.01); *C07C 6/04* (2013.01); *C07C 2521/02* (2013.01); *C07C 2521/06* (2013.01); *C07C 2521/08* (2013.01); *C07C 2521/10* (2013.01); *C07C 2521/18* (2013.01); *C07C 2523/28* (2013.01); *C07C 2523/30* (2013.01); *C07C 2523/36* (2013.01); *C07C 2529/08* (2013.01); *C07C 2529/16* (2013.01); *C07C 2529/40* (2013.01); *C07C 2529/65* (2013.01); *C07C 2529/70* (2013.01); *Y02P 20/52* (2015.11); *Y02P 20/584* (2015.11)

(58) Field of Classification Search
CPC .......... C07C 5/3335; C07C 6/04; B01J 37/08; B01J 37/18; B01J 38/12; B01J 38/02; B01J 21/08; B01J 23/92; B01J 23/30; B01J 29/90; B01J 29/084
See application file for complete search history.

(56) References Cited

U.S. PATENT DOCUMENTS 2,124,566 A * 7/1938 Grosse .................... C07C 5/412
208/121
3,173,855 A 3/1965 Miale et al.
3,175,967 A 3/1965 Miale et al.
(Continued)

FOREIGN PATENT DOCUMENTS

DE 1939270 A1 2/1970
EP 1 129 056 B1 2/2005
(Continued)

OTHER PUBLICATIONS

English-language International Search Report in corresponding PCT/TH2014/000012, dated Jul. 31, 2014.
(Continued)

Primary Examiner — Philip Y Louie
(74) Attorney, Agent, or Firm — Finnegan, Henderson, Farabow, Garrett & Dunner, LLP

(57) ABSTRACT

The invention relates to a process for converting paraffin to olefin comprising the following steps: (a) providing a hydrocarbon feedstock containing at least one paraffin having 1 to 12 carbon atoms and at least one olefin having 2 to 12 carbon atoms; (b) providing a catalyst containing at least one Group VIA and/or Group VIIA transition metal on a solid support; (c) pretreating the catalyst by contacting the catalyst with at least one reducing gas and at least one oxidizing gas; and (d) contacting the by hydrocarbon feedstock and the pretreated catalyst at a temperature in the range of 200° C. to 600° C., preferably 320° C. to 450° C. and to a catalyst for use therein.

19 Claims, No Drawings

(56) References Cited

U.S. PATENT DOCUMENTS

| | | | |
|---|---|---|---|
| 3,321,545 A * | 5/1967 | Rigney | C07C 5/52 |
| | | | 585/257 |
| 3,598,723 A | 8/1971 | Rausch | |
| 3,598,725 A | 8/1971 | Hilfman | |
| 4,323,482 A * | 4/1982 | Stiles | B01J 37/16 |
| | | | 502/240 |
| 4,738,940 A | 4/1988 | Dufresne et al. | |
| 4,956,517 A | 9/1990 | Johnson et al. | |
| 5,171,921 A | 12/1992 | Gaffney et al. | |
| 6,187,985 B1 * | 2/2001 | Le Peltier | B01J 23/622 |
| | | | 585/442 |
| 6,239,057 B1 | 5/2001 | Ichikawa et al. | |
| 6,346,228 B1 | 2/2002 | Choudhary et al. | |
| 6,534,437 B2 | 3/2003 | Eijsbouts et al. | |
| 8,258,357 B2 | 9/2012 | Dukandar et al. | |
| 2006/0183942 A1 * | 8/2006 | Gaffney | B01J 23/002 |
| | | | 562/547 |
| 2008/0154056 A1 * | 6/2008 | Gaffney | C07C 51/215 |
| | | | 558/463 |
| 2008/1016717 | 7/2008 | Malyala et al. | |
| 2008/0188695 A1 * | 8/2008 | Dieterle | B01J 23/96 |
| | | | 568/956 |
| 2009/0145808 A1 | 6/2009 | Choi et al. | |
| 2010/0331592 A1 * | 12/2010 | Sangar | B01J 29/076 |
| | | | 585/420 |
| 2011/1003675 | 2/2011 | White et al. | |
| 2012/0264990 A1 | 10/2012 | Nicholas et al. | |
| 2017/0267609 A1 | 9/2017 | Suriye et al. | |
| 2017/0297980 A1 | 10/2017 | Suriye et al. | |
| 2017/0305816 A1 | 10/2017 | Suriye et al. | |
| 2018/0029024 A1 | 2/2018 | White et al. | |

FOREIGN PATENT DOCUMENTS

| | | |
|---|---|---|
| WO | WO 2010-111199 A2 | 9/2010 |
| WO | WO 2010-111199 A3 | 9/2010 |

OTHER PUBLICATIONS

Written Opinion of the International Searching Authority in the European Patent Office in corresponding PCT/TH2014/000012, dated Jul. 31, 2014.

Non-Final Rejection in U.S. Appl. No. 15/616,975, dated Mar. 8, 2018, (9 pages).

* cited by examiner

PROCESS FOR CONVERTING PARAFFIN TO OLEFIN AND CATALYST FOR USE THEREIN

This is a national stage application under 35 U.S.C. § 371 of International Application No. PCT/TH2014/000012, filed Mar. 28, 2014, and claims priority to European Patent Application No. 13162080,9, filed Apr. 3, 2013, the content of each of which is incorporated herein by reference.

TECHNICAL FIELD

The present invention relates to a process for converting paraffin to olefin and to a catalyst for use therein.

BACKGROUND ART

Olefins have long been desired as feedstock for the petrochemical industries. They are useful in preparing a wide variety of petrochemical goods. Propylene is one of the most important olefin and its demand has grown substantially, largely due to its use as a precursor in the production of polypropylene for packaging materials and other commercial products.

Methods are known for the production of olefins. Currently, the majority of light olefins such as ethylene and propylene are produced during the steam cracking or pyrolysis of hydrocarbon feedstock such as ethane, propane, natural gas, petroleum liquids, naphtha and carbonaceous materials.

Steam cracking involves a very complex combination of reactions and gas recovery systems. It is also highly energy intensive and gives relatively low ethylene and propylene yields. It is known that propylene yield from steam cracking may be improved using metathesis of olefins method.

Olefins metathesis is a known type of reaction in which one or more olefinic compounds are transformed into other olefins of different molecular weights. For example, propylene can be produced from olefins metathesis of feedstock comprising ethylene and butenes. However, this process consumes ethylene and butenes which have many other downstream uses and relatively high commercial value.

Another route for light olefin production is paraffin dehydrogenation. Dehydrogenation process provides better olefin yield than steam cracking but exhibits rapid catalyst coking requiring frequent and costly regeneration. Moreover, the significant capital cost of a propane dehydrogenation plant is normally justified only in cases of large-scale propylene production units (e.g., typically 250,000 metric tons per year or more).

Many approaches for improving light olefins production have been attempted. For example, EP 1,129,056 B1 describes a process for the production of mono-olefins from gaseous paraffinic hydrocarbons by autothermal cracking. The process comprising feeding the paraffinic hydrocarbons feedstock and a molecular oxygen-containing gas to an autothermal cracker wherein they are reacted by oxidative dehydrogenation to form a product comprising one or more mono-olefin(s). This process requires severe operating condition and hence high energy consumption with low olefins yield.

U.S. Pat. No. 5,171,921 describes a process for the production of C2-C5 olefins from higher olefinic or paraffinic or mixed olefin and paraffin feedstock by contacting the higher hydrocarbon feed with a steam activated catalyst containing phosphorous and H-ZSM-5. This process requires high operating temperature up to 700° C.

U.S. Pat. No. 8,258,357 B2 describes an integrated process for production of olefin from C4 feedstock comprising butane which combines a dehydrogenation unit with an olefins metathesis unit. This process requires relatively high operating temperature and consumes high value feedstock materials like hydrogen and ethylene.

It has been observed that the disclosed processes for the manufacture of olefins may have certain disadvantages during its implementation as described above.

DISCLOSURE OF INVENTION

Therefore, it is an object of the present invention to overcome the drawbacks of the prior arts, in particular by providing a process which can effectively convert the relatively low value paraffin to higher value olefin at a mild condition.

The above object is achieved by a process for converting paraffin to olefin comprising the following steps: (a) providing a hydrocarbon feedstock containing at least one paraffin having 1 to 12 carbon atoms and at least one olefin having 2 to 12 carbon atoms; (b) providing a catalyst containing at least one Group VIA and/or Group VIIA transition metal on a solid support; (c) pretreating the catalyst by contacting the catalyst with at least one reducing gas and at least one oxidizing gas; and (d) contacting the hydrocarbon feedstock and the pretreated catalyst at a temperature in the range of 200° C. to 600° C., preferably 320° C. to 450° C.

The term hydrocarbon feedstock in the present invention refers to the total, combined feed; including any recycle hydrocarbon streams, but not including any non-hydrocarbon diluents, which may be added along with the feed according to some embodiments.

It is important for the present invention that the hydrocarbon feedstock is a mixture of at least one paraffin and at least one olefin having the same or different number of carbon atoms. The mixture can be obtained directly from a petrochemical process, for example a 65 mixed C3 stream or a mixed C4 stream from a naphtha cracking process or can be obtained by mixing a paraffin-rich stream with an olefin-rich stream.

It is preferred that the at least one paraffin is methane, ethane, propane, n-butane, i-butane, n-pentane, i-pentane or mixtures thereof, more preferably propane, n-butane, i-butane or mixtures thereof.

It is also preferred that the at least one olefin is ethylene, propylene, 1-butene, cis-2-butene, trans-2-butene, n-pentene or mixtures thereof, more preferably is ethylene.

At least some amount of olefin in the feedstock is necessary to initiate the conversion of paraffin to olefin according to the present invention. The at least one olefin can still be maintained in the feedstock as a co-feed or can also be excluded from the feedstock once the conversion is initiated.

It is preferred that the weight ratio of paraffins to olefins in the hydrocarbon feedstock is in the range of 0.1:1 to 100:1, more preferably 0.5:1 to 10:1.

Catalysts useful in the present invention comprise at least one Group VIA or Group VIIA transition metal on a solid support.

It is preferred that the at least one Group VIA or Group VIIA transition metal is molybdenum, tungsten, rhenium or mixtures thereof, preferably is tungsten.

More preferred is that the catalyst comprises 1 to 15 percent by weight of the at least one Group VIA or Group VIIA transition metal, most preferably 5 to 10 percent by weight, based on total weight of the catalyst.

It is also preferred that the solid support is silicon dioxide, aluminum oxide, activated carbon, magnesium oxide, titanium dioxide, lanthanum oxide, zirconium dioxide, zeolite, layered double hydroxides or any combination thereof, preferably a combination of silicon dioxide and zeolite, more preferably a combination of silicon dioxide and 0.1 to 60 percent by weight of zeolite, based on total weight of the solid support.

Further preferred the zeolite is selected from ZSM-5, X-zeolite, Y-zeolite, beta zeolite, MCM-22, ferrierrite, chabazite or mixtures thereof, preferably is Y-zeolite.

To even further improve efficiency of the process, the catalyst may be mixed or used together with a co-catalyst. Preferably, the catalyst is mixed or used together with isomerization catalyst. Isomerization catalyst can be selected from a group consisting of magnesium oxide, calcium oxide, yttrium oxide, zinc oxide, hydrotalcite and a solid solution of aluminum oxide and magnesium oxide.

The catalyst of the present invention can be prepared by impregnation or partial impregnation method which generally involves contacting the solid support with an impregnation solution of a transition metal compound. The impregnation conditions should be selected to achieve a desired level of transition metal on the catalyst. The preferred conditions include concentration of metal compound in the impregnation solution in the range of $0.1 \cdot 10^{-6}$ M to 5 M, impregnation temperature in the range of 20° C. to 200° C. and contact time in the range of 1 minute to 5 hours. Other known methods for catalyst preparation such as incipient wetness, ion exchange or the like can also be used.

The impregnation solution includes at least one transition metal compound in at least one solvent. Many selections of transition metal compound are possible for the present invention such as nitrate, sulfate or carbonate of the transition metal. For example, the transition metal compound used in the catalyst preparation step is ammonium metatungsten tetrahydrate.

The selected solvent for the present invention can be any suitable solvent which can dissolve or disperse the selected metal compounds such as oxygenated solvent and hydrocarbon solvent. For example, the solvent can be selected from water, methanol, ethanol and hexane.

Following impregnation (or other preparation methods as mentioned above), the metal deposited support is preferably dried and then calcined to remove moisture and volatile fractions of the metal compound used in the catalyst preparation step. Drying conditions generally include a temperature from 20° C. to 200° C. and a period from 2 hours to 20 hours. Calcining conditions generally include a temperature from 200° C. to 800° C. and a period of 1 hour to 48 hours. Both drying and calcining steps are normally performed under an atmosphere of oxygen-containing gas (e.g., air or oxygen). It should be pointed out that the drying step can be combined with the calcining step, i.e. drying occurs during calcinations.

Prior to its use in the conversion reaction, the catalyst is pretreated with reducing gas and oxidizing gas. The use of such catalyst pretreatment results in formation of metal hydride and metal oxide. A suitable amount of metal hydride and metal oxide on the catalyst is preferred to make the catalyst active in the conversion of paraffin to olefin according to the present invention. A proper amount of metal hydride and metal oxide can be achieved by selecting suitable conditions for catalyst pretreatment. That is, it is preferred that the pretreated catalyst comprises a mixture of at least one transition metal hydride and at least one transition metal oxide.

It is preferred that pretreating the catalyst comprises contacting the catalyst with the at least one reducing gas, preferably hydrogen, at a temperature in the range of 200° C. to 700° C., preferably 300° C. to 600° C., preferably with a WHSV in the range of 0.0001 hr$^{-1}$ to 100 hr$^{-1}$, more preferably 0.001 hr$^{-1}$ to 10 hr$^{-1}$, and preferably for a period of 5 minutes to 30 hours, more preferably 12 hours to 24 hours.

It is also preferred that pretreating the catalyst comprises contacting the catalyst with the at least one oxidizing gas, preferably air, at a temperature in the range of 200° C. to 700° C., preferably 300° C. to 600° C., preferably with a WHSV in the range of 0.0001 hr$^{-1}$ to 100 hr$^{-1}$, more preferably 0.001 hr$^{-1}$ to 10 hr$^{-1}$, and preferably for a period of 5 minutes to 30 hours, more preferably 12 hours to 24 hours.

As is understood in the art, the WHSV is the mass flow of the hydrocarbon feedstock divided by the weight of the catalyst bed and represents the equivalent mass of feed processed every hour. The WHSV is related to the inverse of the reactor residence time.

In a preferred embodiment, the catalyst is first contacted with a reducing gas and afterwards contacted with an oxidizing gas. In a further preferred embodiment, the catalyst is first contacted with an oxidizing gas and then contacted with a reducing gas.

The reducing gas and the oxidizing gas can optionally be diluted with diluents. The diluents should be nonreactive under the selected catalyst pretreatment condition. Suitable diluents are, for example, nitrogen, argon, methane and the like, or mixtures thereof. The catalyst pretreatment may occur shortly prior to use or in situ.

Following the catalyst pretreatment, the pretreated catalyst is then exposed to flowing hydrocarbon feedstock in the reaction zone at proper conditions to start the conversion of paraffin to olefin.

Contacting the hydrocarbon feedstock with the pretreated catalyst can occur continuously or batch wise. Generally, the contacting is performed with the hydrocarbon feedstock being passed continuously through a fixed bed of the catalyst in the reaction zone. A number of other suitable systems for carrying out the feedstock/catalyst contacting are known in the art, with the optimal choice depending on the particular feedstock, rate of catalyst deactivation and other factors. Such systems include moving bed system, swing bed system and fluidized bed system.

It is preferred that contacting the hydrocarbon feedstock and the pretreated catalyst in step (d) is carried out at a temperature in the range of 320° C. to 450° C.

It is also preferred that contacting the hydrocarbon feedstock and the pretreated catalyst in step (d) is carried out at a pressure in the range of 1 bar to 60 bar, preferably 20 bar to 40 bar.

It is also further preferred that contacting the hydrocarbon feedstock and the pretreated catalyst in step (d) s carried out at a WHSV in the range of 0.01 hr$^{-1}$ to 200 hr$^{-1}$, preferably 0.05 hr$^{-1}$ to 100 hr$^{-1}$, more preferably 0.1 hr$^{-1}$ to 20 hr$^{-1}$.

Under the conversion conditions described above, the hydrocarbon feedstock is normally in the gas-phase in the reaction zone. However, the conversion reaction can also occur when the hydrocarbon feedstock is in liquid phase or mixture of gas and liquid phase.

It is normal to have separation unit(s) downstream of the reaction zone in order to separate and achieve the desired purity of the products from the conversion process.

Recycling of the unconverted hydrocarbon feedstock to the reaction zone may often be desirable for achieving complete or at least significantly higher overall conversion than the equilibrium-limited per pass conversion of the feedstock.

The catalyst employed in the inventive process normally losses its activity over time due to the buildup of poisonous substances, coke, carbon and/or polymer on the catalyst process, and hence requires regeneration.

Therefore, it is preferred that the process according to the present invention further comprises a regeneration step as step (e) of the process.

Regeneration typically involves removing the poisonous substances, coke, carbon and/or polymer deposited on catalyst surface by oxidative burning.

Preferably, the regeneration step (e) comprises contacting the catalyst with at least one oxidizing gas, preferably air, at a temperature in the range of 200° C. to 700° C., preferably 400° C. to 550° C.

Surprisingly, it was found that the inventive process provides an improved, more economical and efficient process for converting paraffin to olefin.

The examples below demonstrate the advantages achieved from using the process of the invention in paraffin to olefin conversion by showing the surprising effects of certain steps and conditions of the process, in particular by providing a process which can effectively convert the relatively low value paraffin to higher value olefin at a mild condition.

The following examples are intended to be illustrative of this invention only. They are not to be taken in any way limiting on the scope of this invention. Numerous changes and modifications can be made without departing from the scope of the invention as disclosed in the accompanying claims.

EXAMPLES

Examples 1 to 6 are illustrative of the process for converting paraffin to olefin according to this invention.

Example 1

3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 $hr^{-1}$ for 4 hours, then subsequently flow 10 percent by volume of hydrogen gas balancing with nitrogen through the catalyst bed at a temperature of 400° C. and WHSV 0.002 $hr^{-1}$ for 1 hour and then raised temperature to 550° C. and hold for 2 hours before cooling down to reaction temperature at 350° C.

When bed temperature reached 350° C., feedstock containing 10 percent by weight of n-butane and 20 percent by weight of ethylene balancing with nitrogen was fed through the catalyst bed at flow rate 10-20 cc/min and pressure 20 barg.

Effluents from the reaction were directed to GC-FID (Agilent) to measure their chemical compositions. The measured compositions of effluents were used to calculate paraffin conversions and olefin yields. The result of this experiment is shown in Table 1.

Example 2

An experiment the same as in Example 1 was performed with a feedstock containing 10 percent by weight of i-butane and 20 percent by weight of ethylene balancing with nitrogen. The result of this experiment is shown in Table 1.

Example 3

An experiment the same as in Example 1 was performed with a feedstock containing 10 percent by weight of propane and 20 percent by weight of ethylene balancing with nitrogen. The result of this experiment is shown in Table 1.

Example 4

An experiment the same as in Example 1 was performed with a feedstock containing 10 percent by weight of LPG (containing 25 wt % propane, 25 wt % i-butane and 50 wt % n-butane) and 20 percent by weight of ethylene balancing with nitrogen. The result of this experiment is shown in Table 1.

Example 5

3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 $hr^{-1}$ for 4 hours, then subsequently flow 10 percent by volume of hydrogen gas balancing with nitrogen through the catalyst bed at a temperature of 400° C. and WHSV 0.002 $hr^{-1}$ for 1 hour and then raised temperature to 550° C. and hold for 2 hours before cooling down to reaction temperature at 350° C.

When bed temperature reached 350° C., feedstock containing 4 percent by weight of n-butene and 6 percent by weight of n-butane and 20 percent by weight of ethylene balancing with nitrogen was fed through the catalyst bed at flow rate 5-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Example 6

This example is illustrative of the process for converting paraffin to olefin according to this invention.

An experiment the same as in Example 1 was performed without magnesium oxide. The result of this experiment is shown in Table 1.

Comparative examples A and B illustrate the effect of catalyst pretreatment conditions on the inventive process.

Comparative Example A 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing 10 percent by volume of hydrogen gas balancing with nitrogen through the catalyst bed at a temperature of 400° C. and WHSV 0.002 hr$^{-1}$ for 1 hour, and then raised temperature to 550° C. and hold for 2 hours before cooling down to reaction temperature at 350° C.

When bed temperature reached 350° C., feedstock containing 10 percent by weight of n-butane and 20 percent by weight of ethylene balancing with nitrogen was fed through the catalyst bed at flow rate 10-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Comparative Example B 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 hr$^{-1}$ for 4, and then raised temperature to 550° C. and hold for 2 hours before cooling down to reaction temperature at 350° C. When bed temperature reached 350° C., feedstock containing 10 percent by weight of n-butane and 20 percent by weight of ethylene balancing with nitrogen was fed through the catalyst bed at flow rate 10-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Comparative examples C, D, E and F illustrate the effect of olefin co-feeding on the inventive process.

Comparative Example C 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 hr$^{-1}$ for 4 hours, then subsequently flow 10 percent by volume of hydrogen gas balancing with nitrogen through the catalyst bed at a temperature of 400° C. and WHSV 0.002 hr$^{-1}$ for 1 hour and then raised temperature to 550° C. and hold for 2 hours before cooling down to reaction temperature at 350° C.

When bed temperature reached 350° C., feedstock containing 10-20 percent by weight of n-butane balancing with nitrogen was fed through the catalyst bed at flow rate 5-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Comparative Example D 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 hr$^{-1}$ for 4 hours, then subsequently flow 10 percent by volume of hydrogen gas balancing with nitrogen through the catalyst bed at a temperature of 400° C. and WHSV 0.002 hr$^{-1}$ for 1 290 hour and then raised temperature to 550° C. and hold for 2 hours before cooling down to reaction temperature at 350° C.

When bed temperature reached 350° C., feedstock containing 10-20 percent by weight of ethylene balancing with nitrogen was fed through the catalyst bed at flow rate 5-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Comparative Example E 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 hr$^{-1}$ for 4 hours, then subsequently flow 10 percent by volume of hydrogen gas balancing with nitrogen through the catalyst bed at a temperature of 400° C. and WHSV 0.002 hr$^{-1}$ for 1 hour and then raised temperature to 550° C. and hold for 2 hours before cooling down to reaction temperature at 350° C.

When bed temperature reached 350° C., feedstock containing 10-20 percent by weight of i-Butane balancing with nitrogen was fed through the catalyst bed at flow rate 5-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

Comparative Example F 3 grams of catalyst comprising 8 percent by weight of tungsten on a solid support comprising 5 percent by weight of HY-zeolite and 95 percent by weight of silicon dioxide was mixed with 3 grams of magnesium oxide and then packed in a tubular reactor.

After that the catalyst was pretreated by flowing air through the catalyst bed at a temperature of 500° C. and WHSV 0.30 hr$^{-1}$ for 4 hours, then subsequently flow 10 percent by volume of hydrogen gas balancing with nitrogen through the catalyst bed at a temperature of 400° C. and WHSV 0.002 hr$^{-1}$ for 1 hour and then raised temperature to 550° C. and hold for 2 hours before cooling down to reaction temperature at 350° C.

When bed temperature reached 350° C., feedstock containing 10-20 percent by weight of propane balancing with nitrogen was fed through the catalyst bed at flow rate 5-20 cc/min and pressure 20 barg.

Effluents from the reaction were directed to GC-FID (Agilent) to measure their chemical compositions. The measured compositions of effluents were used to calculate paraffins conversion and olefins yield. The result of this experiment is shown in Table 1.

TABLE 1

| Example | Feed | Co-catalyst | Pretreatment | Paraffin(s) Conversion (wt %) | Ethylene Selectivity (wt %) | Propylene Selectivity (wt %) |
|---|---|---|---|---|---|---|
| Example 1 | n-Butane Ethylene | MgO | Air, H2 | 60 | 70 | 25 |
| Example 2 | i-Butane Ethylene | MgO | Air, H2 | 57 | 82 | 10 |
| Example 3 | Propane Ethylene | MgO | Air, H2 | 40 | 8 | 80 |
| Example 4 | LPG Ethylene | MgO | Air, H2 | 55 | 20 | 70 |
| Example 5 | n-Butene n-Butane Ethylene | MgO | Air, H2 | 90 wt % of C4 hydrocarbon in feedstock (n-Butene and n-Butane) was converted to a product stream containing 64 wt % ethylene and 27 wt % propylene | | |
| Example 6 | n-Butane Ethylene | None | Air, H2 | 66% | 72% | 25% |
| Comparative Example A | n-Butane Ethylene | MgO | H2 | No paraffin conversion. 40% of olefin was converted to 60 wt % propylene and 40 wt % n-butene | | |
| Comparative Example B | n-Butane Ethylene | MgO | Air | No Reaction | | |
| Comparative Example C | n-Butane | MgO | Air, H2 | No Reaction | | |
| Comparative Example D | Ethylene | MgO | Air, H2 | No Reaction | | |
| Comparative Example E | i-Butane | MgO | Air, H2 | No Reaction | | |
| Comparative Example F | Propane | MgO | Air, H2 | No Reaction | | |

The paraffin conversions shown in Table 1 were calculated from weight of paraffin(s) converted during reaction divided by total weight of paraffin(s) in feedstock and then multiplies by one hundred. The ethylene and propylene selectivity shown in Table 1 were calculated from weight of ethylene or propylene produced from the reaction divided by weight of all products produced from the reaction and then multiplies by one hundred. The features disclosed in the foregoing description and in the claims may, both separately and in any combination thereof, be material for realizing the invention in diverse forms thereof.

The invention claimed is:

1. A process for converting paraffin to olefin comprising the following steps:
    (a) providing a hydrocarbon feedstock containing at least one paraffin having 1 to 12 carbon atoms and at least one olefin having 2 to 12 carbon atoms;
    (b) providing a catalyst containing a single metal on a solid support, wherein the single metal is a Group VIA transition metal;
    (c) pretreating the catalyst by contacting the catalyst with at least one reducing gas and at least one oxidizing gas; and
    (d) contacting the hydrocarbon feedstock with the pretreated catalyst at a temperature in the range of 200° C. to 600° C. to thereby form ethylene and propylene with a selectivity for ethylene and propylene of at least 88 wt %.

2. The process according to claim 1, wherein the at least one paraffin is methane, ethane, propane, n-butane, i-butane, n-pentane, i-pentane or mixtures thereof.

3. The process according to claim 1, wherein the at least one olefin is ethylene, propylene, 1-butene, cis-2-butene, trans-2-butene, n-pentene or mixtures thereof.

4. The process according to claim 1, wherein the weight ratio of paraffins to olefins in the hydrocarbon feedstock is in the range of 0.1:1 to 100:1.

5. The process according to claim 1, wherein the Group VIA transition metal is molybdenum or tungsten.

6. The process according to claim 1, wherein the catalyst comprises 1 to 15 percent by weight of the Group VIA transition metal based on total weight of the catalyst.

7. The process according to claim 1, wherein the solid support is silicon dioxide, aluminum oxide, activated carbon, magnesium oxide, titanium dioxide, lanthanum oxide, zirconium dioxide, zeolite, layered double hydroxides or any combination thereof.

8. The process according to claim 1, wherein pretreating the catalyst comprises contacting the catalyst with the at least one reducing gas at a temperature in the range of 200° C. to 700° C.

9. The process according to claim 8, wherein the reducing gas is hydrogen.

10. The process according to claim 8, wherein the contacting the catalyst with the at least one reducing gas is done with a WHSV in the range of 0.0001 hr$^{-1}$ to 100 hr$^{-1}$ for a period of 5 minutes to 30 hours.

11. The process according to claim 1, wherein pretreating the catalyst comprises contacting the catalyst with the at least one oxidizing gas at a temperature in the range of 200° C. to 700° C.

12. The process according to claim 11, wherein the oxidizing gas is air.

13. The process according to claim 11, wherein the contacting the catalyst with the at least one oxidizing gas is done with a WHSV in the range of 0.0001 hr$^{-1}$ to 100 hr$^{-1}$ for a period of 5 minutes to 30 hours.

14. The process according to claim 1, wherein the pretreated catalyst comprises a mixture of at least one transition metal hydride and at least one transition metal oxide.

15. The process according to claim 1, wherein contacting the hydrocarbon feedstock with the pretreated catalyst in step (d) is carried out at a pressure in the range of 1 bar to 60 bar.

16. The process according to claim 1, wherein contacting the hydrocarbon feedstock and the pretreated catalyst in step (d) is carried out at a WHSV in the range of 0.01 $hr^{-1}$ to 200 $hr^{-1}$.

17. The process according to claim 1, wherein the process further comprises a regeneration step (e).

18. The process according to claim 17, wherein the regeneration step (e) comprises contacting the catalyst with at least one oxidizing gas at a temperature in the range of 200° C. to 700° C.

19. The process according to claim 1, wherein the selectivity for ethylene and propylene ranges from 88 wt % to 97 wt %.

* * * * *